United States Patent
Kyriakou

(10) Patent No.: US 8,792,702 B2
(45) Date of Patent: Jul. 29, 2014

(54) METHOD FOR PROVIDING A 3D IMAGE DATA RECORD WITH SUPPRESSED ALIASING ARTIFACTS OVERLAPPING THE FIELD OF VIEW AND COMPUTED TOMOGRAPH

(75) Inventor: Yiannis Kyriakou, Spardorf (DE)

(73) Assignee: Siemens Aktiengesellschaft, Munich (DE)

( * ) Notice: Subject to any disclaimer, the term of this patent is extended or adjusted under 35 U.S.C. 154(b) by 151 days.

(21) Appl. No.: 13/470,384

(22) Filed: May 14, 2012

(65) Prior Publication Data

US 2012/0294501 A1 Nov. 22, 2012

(30) Foreign Application Priority Data

May 16, 2011 (DE) .......................... 10 2011 075 917

(51) Int. Cl.
*G06K 9/00* (2006.01)
(52) U.S. Cl.
USPC .......................................................... 382/131
(58) Field of Classification Search
None
See application file for complete search history.

(56) References Cited

U.S. PATENT DOCUMENTS

| 2003/0095694 A1* | 5/2003 | Dinstein et al. ............... 382/128 |
| 2006/0274061 A1* | 12/2006 | Wang et al. ................... 345/420 |
| 2007/0195923 A1 | 8/2007 | Netsch |
| 2010/0128953 A1* | 5/2010 | Ostrovsky-Berman ....... 382/131 |
| 2010/0322498 A1* | 12/2010 | Wieczorek et al. ........... 382/131 |
| 2011/0150306 A1* | 6/2011 | Ross et al. .................... 382/131 |

OTHER PUBLICATIONS

Feldkamp et al.; Practical Cone-beam Algorithm, JOSA A1, 612 (1984) J. Opt. Soc. Amer. A, vol. 1, No. 6, Jun. 1984, Seiten 612-619; Journal of the Optical Society of America; Magazine; 1984.
A. C. Kak et al. Principles of Computerized Tomographic Imaging Kapitel 3, Algorithms for Reconstruction with Nondiffracting Sources; IEEE Press, New York, 1988, pp. 49-112; Others; 1988; US.
Sourbelle et al.; Reconstruction from truncated projections in CT using adaptive detruncation European Radiology vol. 15, No. 5, May 2005, Seite 1008-1014; Magazine; 2005.
A novel reconstruction algorithm to extend the CT scan field-of-view, J. Hsieh, E. Chao, J. Thibault, B. Grekowicz, A. Horst, S. McOlash, T.J. Myers Medical Physics, vol. 31, No. 9, Sep. 2004, pp. 2385-2391; Others; 2004.
Willi A. Kalender et al., Flat-detector computed tomography (FD-CT), Eur Radiol (2007) 17: pp. 2767-2779 Published online: Jun. 23, 2007; Magazine; 2007.

(Continued)

*Primary Examiner* — Nirav G Patel

(57) ABSTRACT

A method is provided for providing a 3D image data record relating to a biological object with suppressed aliasing artifacts overlapping the field of view caused by an incomplete geometric capture of the object by a computed tomography. A first 3D image data record is provided to describe a subarea of the object. A second 3D image data record is obtained by the computed tomography including data relating to the subarea of the object and is registered with the first 3D image data record. Data of the second 3D image data record is extended and/or amended according to data of the first 3D image data record. A part of such data of the second 3D image data record can be assigned to an aliasing artifact overlapping the field of view and thus generates a modified second 3D image data record with suppressed aliasing artifacts overlapping the field of view.

8 Claims, 2 Drawing Sheets

(56) References Cited

OTHER PUBLICATIONS

K. P. Anoop et al., Estimation of Missing Data using Windowed Linear Prediction in Laterally Truncated Projections in Cone-Beam CT Proceedings of the 29th Annual International Conference of the IEEE EMBS, Engineering in Medicine and Biology Society, Cité Internationale, Lyon, France Aug. 23-26, 2007 pp. 2903-2906; Others; 2007.

Jonathan S. Maltz et al. CT Truncation artifact removal using water-equivalent thicknesses derived from truncated projection data Proceedings of the 29th Annual International Conference of the IEEE EMBS, Engineering in Medicine and Biology Society, Cité Internationale, Lyon, France Aug. 23-26, 2007 pp. 2907-2911; Others; 2007.

Jared Starman et al., Estimating 0th and 1st Moments in C-Arm CT Data for Extrapolating Truncated Projections Medical Imaging 2005: Image Processing, Proc. of SPIE vol. 5747, pp. 378-387; Others; 2005.

Alexander A. Zamyatin et al., Extension of the reconstruction field of view and truncation correction using sinogram decomposition Med. Phys. 34 (5), May 2007, pp. 1593-1604; Magazine; 2007.

D. Kolditz et al.: "Comparison of extended field-of-view reconstructions in C-arm flat-detector CT using patient size, shape or attenuation information", Physics in Medicine and Biology 56 (2011), p. 39-56; Others; 2011.

* cited by examiner

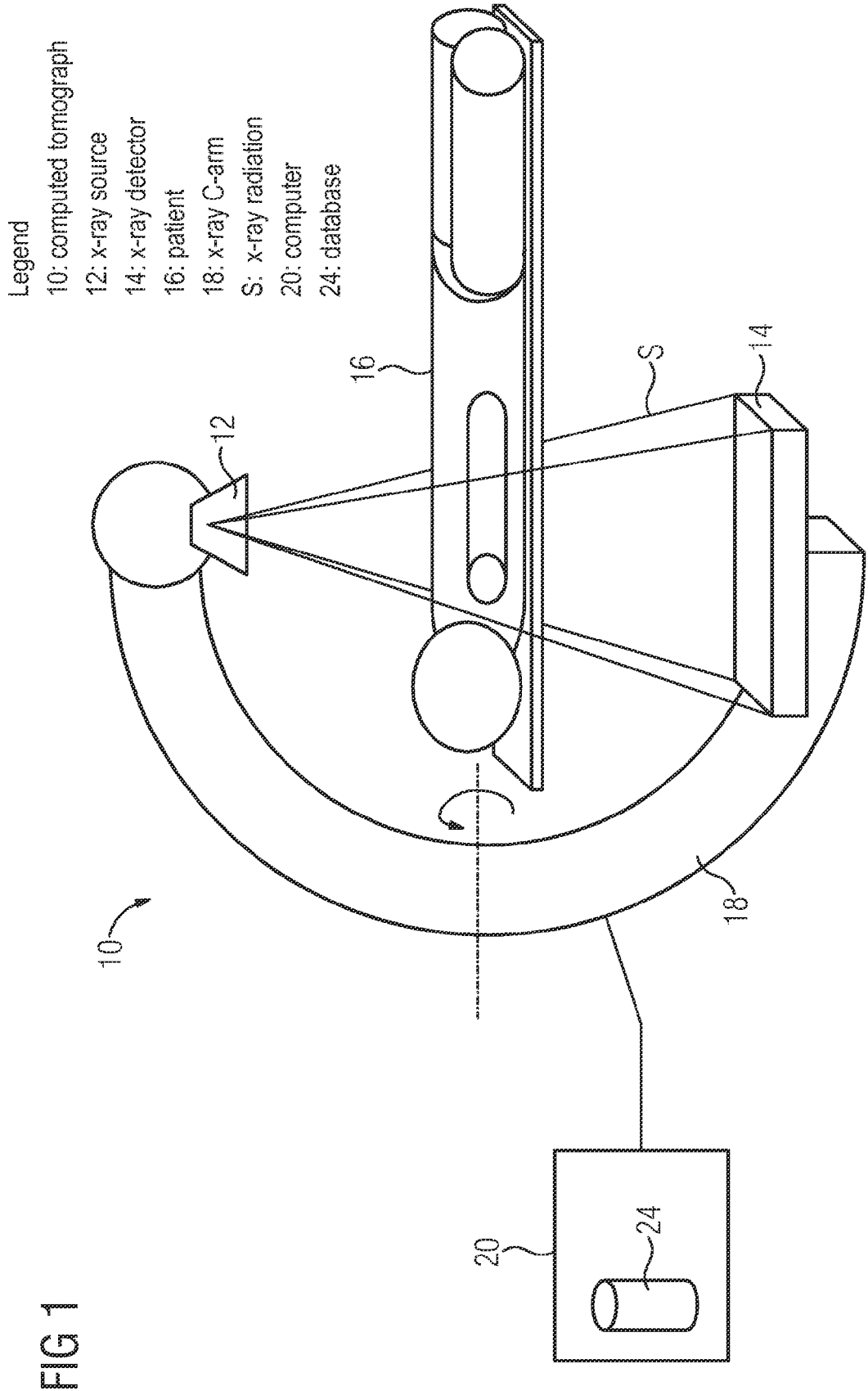

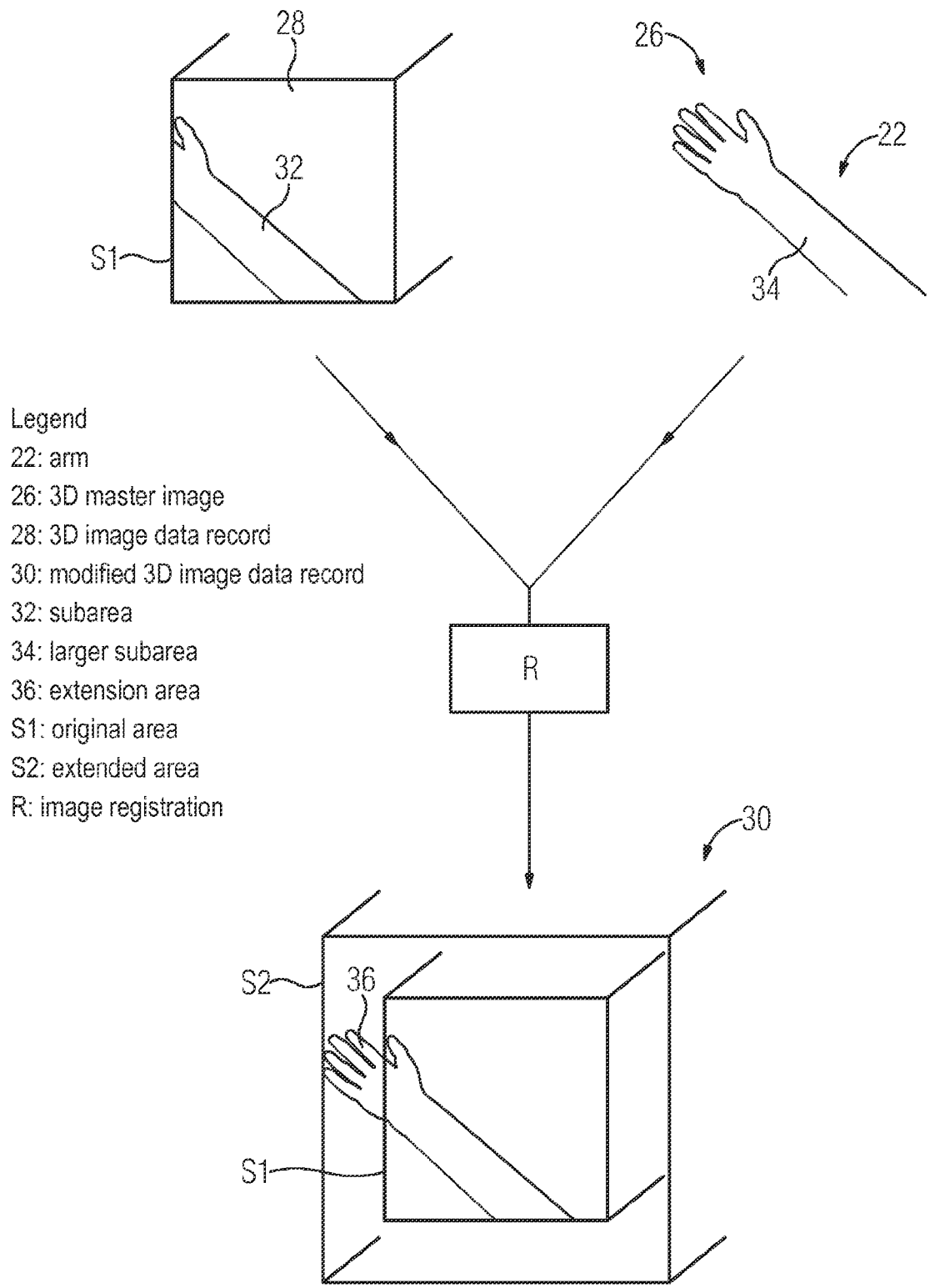

METHOD FOR PROVIDING A 3D IMAGE DATA RECORD WITH SUPPRESSED ALIASING ARTIFACTS OVERLAPPING THE FIELD OF VIEW AND COMPUTED TOMOGRAPH

CROSS REFERENCE TO RELATED APPLICATION

This application claims priority of German application No. 10 2011 075 917.4 filed May 16, 2011, which is incorporated by reference herein in its entirety.

FIELD OF INVENTION

The invention relates to a method for providing a 3D image data record relating to a biological object with suppressed aliasing artifacts overlapping the field of view, which are caused by an incomplete geometric capture of the biological object by means of a computed tomograph. The invention also relates to a computed tomograph having an x-ray source, a detector and an image evaluation apparatus, which is embodied to execute such a method.

BACKGROUND OF INVENTION

The x-ray and/or tomography images obtained by x-ray image recording apparatuses, in particular computed tomographs, may comprise various image artifacts. One type of image artifact is used such that the measured object is not completely captured during the measuring process in terms of its geometric extension. Part of the object under measurement is positioned outside of the field of view and is in this manner truncated, so to speak, in respect of the image obtained therefrom. The image artifacts resulting herefrom can be referred to below as aliasing artifacts overlapping the field of view. They play an essential role particularly in computed tomographs, since a three-dimensional image obtained by means of back projection is frequently based on a plurality of projection images, not all of which capture the object to be measured wholly or completely. The object is not constantly completely within the field of view, namely during the measuring process.

This unwanted data shortening may be meaningful in the case of all computed tomographical scan apparatuses, but nevertheless plays a significant roll particularly with flat panel computed tomographs (see "W. A. Kalender and Y. Kyriaku. Flat-detector CT. Eur Radiol. (11):2767-79, 2007"). With flat panel detector computed tomographs, the view field and/or field of view of the detector which can be captured during the measurement only amounts to approximately 20-25 cm in terms of diameter. This restriction makes the prevention of aliasing artifacts overlapping the field of view almost impossible. Aliasing artifacts overlapping the field of view significantly impair the quality of a resulting x-ray and/or tomography image. The artifacts not only herewith appear in the vicinity of the image edge, but instead also influence central areas of the recorded image.

Aliasing artifacts overlapping the field of view would then not occur for instance if the x-ray radiation was not attenuated at all border areas of the field of view. A defined transition in respect of the absorption values to zero then results. If this transition is however not correctly given, this results during the computed tomography recordings particularly after filtered back projection (see for instance "A. C. Kak and M. Slaney. Principles of Computerized Tomographic Imaging. IEEE Press, 1988", "L. A. Feldkamp, L. C. Davis, and J. W. Kress. Practical cone-beam algorithm. J. Opt. Soc. Am. A, 1(6):612-619, 1984") in the effect that aliasing artifacts overlapping the field of view appear and an apparent increase in the x-ray radiation attenuation values to the image borders is observed. A pale white ring appears in the computed tomography image beyond the border of the field of view. Strip-like artifacts also result outside of the actual field of view area.

Aliasing artifacts overlapping the field of view are generally suppressed such that image areas at the edge of the field of view, to which attenuation values greater than zero are assigned, are extrapolated such that a smoothed value curve is produced toward the x-ray absorption value zero. According to a known method, the truncation areas are extrapolated in the computed tomography projection images used for the back projection onto an attenuation value of zero and it is only then that the filtered back projection is implemented. Within the scope of this extrapolation method, objects are approached for instance by means of a water cylinder (see "Hsieh J, Chao E, Thibault J, Grekowicz B, Horst A, McOlash S and Myers T J, 2004, A novel reconstruction algorithm to extend the CT scan field-of-view Med. Phys. 31, 2385-91"). The patient as a whole can also be approximated as a water ellipsoid, so that in this manner data exists for the extrapolation (see "Maltz J S, Bose S, Shukla H P and Bani-Hashemi A R, 2007, CT truncation artifact removal using water-equivalent thicknesses derived from truncated projection data Proc. IEEE Eng. Med. Biol., Soc. 2007. 2907-11"). A square extrapolation is for instance known from "Sourbelle K, Kachelrieβ M and Kalender W A, 2005, Reconstruction from truncated projections in CT using adaptive detruncation Eur. Radiol. 15, 1008-14", while a so-called sinogram interpolation is described in "Zamyatin A A and Nakanishi S, 2007, Extension of the reconstruction field of view and truncation correction using sinogram decomposition Med. Phys. 34, 1593-604". Further extrapolation methods are known from the following publications: "Janoop K P and Rajgopal K, 2007, Estimation of missing data using windowed linear prediction in laterally truncated projections in cone-beam CT Proc. IEEE Eng. Med. Biol. Soc. 2007, 2903-6", "Starman J, Pelc N, Strobe N and Fahrig R, 2005, Estimating $0^{th}$ and $1^{st}$ moments in C-arm CT data for extrapolating truncated projections Proc. SPIE 5747, 378-87" and "Sourbelle K, Kachelrieβ M and Kalender W A, 2005, Reconstruction from truncated projections in CT using adaptive detruncation Eur. Radiol. 15, 1008-14".

The methods known from the prior art have the objective of improving the image quality within the field of view area, but nevertheless impairing an image modification or quality improvement outside of the field of view area. In the event that several border areas are truncated in the computed tomography projection images, further serious disadvantages result. With the majority of methods, at least one non-truncated projection image is needed in order to ensure the fulfillment of a consistency criterion. A conversion from 3D into 2D data is frequently extremely time-consuming. Extremely shortened data records, such as are the rule with flat panel computed tomographs, cannot be overcome by the usual methods with respect to the aliasing artifacts overlapping the field of view. In addition, anatomical information is frequently lost. The contour of a patient is generally not correctly reproduced, which hampers a treating physician during an operation for instance, when navigating instruments in the body of the patient with the aid of the computed tomography image.

SUMMARY OF INVENTION

It is the object of the invention to provide a method and an x-ray image recording apparatus with which aliasing artifacts overlapping the field of view can still be better suppressed.

This object is achieved by a method and a computed tomography which comprise the features of the claims.

The inventive method is used to provide a 3D data record relating to a biological object with suppressed aliasing artifacts overlapping the field of view, which are caused by an incomplete geometric detection of the biological object by means of a computed tomograph. It includes the following steps:

a) providing at least one first 3D image data record to describe at least one subarea of the biological object;
b) obtaining a second 3D image data record with respect to the biological object by means of a computed tomograph, wherein the second 3D image data record includes data relating to the at least one subarea of the biological object described by the first 3D image data record;
c) registering the first 3D image data record with the second 3D image data record;
d) extending and/or amending the second 3D image data record as a function of data of the first 3D image data record for at least one part of such data of the second 3D image data record, which can be assigned to an aliasing artifact overlapping the field of view and thus generating a modified second 3D image data record with suppressed aliasing artifacts overlapping the field of view.

If the second 3D image data record obtained on the biological object is to be incomplete with respect to the geometric capture of the biological object, this is in particular a cause of aliasing artifacts overlapping the field of view occurring in the resulting computed tomography images. By providing the at least one first 3D image data record, incomplete data can then in particular be extended in the second 3D image data record such that the aliasing artifacts overlapping the field of view are suppressed or even completely prevented. By means of the first 3D image data record, the appearance of aliasing artifacts overlapping the field of view is already prevented so that if necessary, a subsequent modification and/or processing of a resulting computed tomography image can be omitted with respect to the retouching of aliasing artifacts overlapping the field of view. The method therefore does not suppress aliasing artifacts overlapping the field of view by processing the image of a resulting image but instead assesses in advance, by extending the data structure underlying the image so that the artifacts do not appear in the first place. The provision of a concrete first 3D image data record dispenses with imprecise and rough assumptions for the modification of the second 3D image data record. A qualitatively improved and modified second 3D image data record is thus available, from which meaningful computed tomography images can be obtained. Aliasing artifacts overlapping the field of view are prevented very efficiently. Assessing the resulting computed tomography images is thus easier for a person.

Provision can be made in particular for several 3D image data records to be obtained for instance by means of the computed tomograph in order to describe several projection images of the biological object and then the second 3D image data record is obtained with the aid of these 2D image data records by means of back projection. In particular, provision can be made for the first 3D image data record to provide an image model of the biological object. Registration is in particular understood to mean the image registration of the first 3D image data record with the second 3D image data record. This may in particular result in the assignment of the first and second 3D image data record which is correct in terms of position and/or form, for instance by way of a suitable coordinate transformation. The extension and/or amending of the data of the second 3D image data record can either take place directly by means of the data of the first 3D image data record or new data can however be obtained on the basis of the data of the first 3D image data record, with the aid of which the data of the second 3D image data record is extended and/or amended. Data of the second 3D image data record, which can be assigned to an aliasing artifact overlapping the field of view, may in particular be such data which can be assigned to a border area of the image, which is described by the 3D image data record.

The method preferably includes the further step of obtaining a 2D image data record from the modified second 3D image data record and herefrom a computed tomography image, in particular a forward projection image and/or an x-ray sectional image is generated. Forward projection images and x-ray sectional images allow a meaningful interpretation of the measuring data by means of an operating person. Since, within the scope of the method, aliasing artifacts overlapping the field of view in such 2D images are prevented particularly effectively, a very realistic image of the actual characteristics of the measuring object is obtained.

Step c) preferably includes the following sub-steps:
c1) assigning data of the first 3D image data record to data of the second 3D image data record in a fashion which is correct in terms of position and dimension;
c2) determining a comparison value, which is a measure of the degree of the match between the data assigned to one another in step c1). The comparison value can be in particular a similarity value in respect of an image comparison of the image assigned to the first 3D image data record and of the image assigned to the second 3D image data record. In order to determine the similarity of two images, methods known from the prior art can be used;
c3) modifying the data of the first 3D image data record assigned to the second 3D image data record in step c1) such that the comparison value changes compared with the comparison value determined in step c2) such that the degree of matching increases, particularly by amending the first 3D image data record with the aid of draw points. Provision can in particular be made for the first 3D image data record to be modified such that it compares at least a sub-quantity of the second 3D image data record in respect of its image similarity. This can take place for instance in particular pixel by pixel or voxel by voxel, wherein the gray-scale value deviation in the two image data records can be used as a comparison value. Images of an object with a specific contour can be assigned in particular to the 3D image data records, wherein this contour can be provided with draw points at specific points. Provision can then be made for the contour of the image described by the first 3D image data record preferably to be changeable in terms of image in the vicinity of the draw points. Draw points may in particular be understood to mean anchor points in a vector-graphical representation of the image assigned to the first 3D image data record;
c4) preferably repeating steps c1) to c3).

The approximation of the first 3D image data record to the second 3D image data record preferably therefore takes place iteratively. In this way, deviations in respect of the shape and design of a mirroring image object in the first 3D image data record can be adjusted such that the image registration in the second 3D image data record is optimized. The extension and/or amendment of the second 3D image data record then take place in an even more realistic fashion.

The first 3D image data record provided in step a) is preferably obtained with the following sub-steps:
Providing at least two image data records relating to at least two comparison objects, which are embodied in a similar or identical fashion to the object.

Determining the first 3D data record in order to describe the at least one subarea of the biological object by obtaining an averaged effective image data record from the at least two image data records.

Biological objects of the same type (e.g. hand, hip, etc.) usually indicate variations from living being to living being. It is therefore advantageous to provide an averaged image of the biological object in order to be able to amend or extend the second 3D image data record in a very universal fashion. Faults in the visual description of the biological object are kept to a minimum. The first 3D image data record may then be assigned in particular to a statistical shape model of an anatomical structure.

The at least two image data records of the at least two comparison objects are then preferably created with the aid of computed tomography images of real comparison objects, wherein a segmentation of the computed tomography images is implemented in the creation step. Real comparison objects may in particular be real body parts of living beings, from which image data is obtained. This image data can then be processed such that an average image is generated from the individual images which then forms the basis of the first image data record. A first 3D image data record is herewith created, which reproduces the real situation very well. Alternatively, provision can however also be made for the first 3D image data record to be obtained with the aid of an image simulation method, e.g. a method of constructive solid body geometry (e.g. CAD). Computed tomography and/or magnetic resonance data may form the basis of the first 3D image data record.

A database with at least two different 3D image data records is preferably provided in step a), which describe different subareas of a biological object or different biological objects. For instance, the database may include different 3D image data records relating to different body parts. The image registration can then take place such that the most suitable 3D image data record is selected from the 3D image data records available in the database, i.e. that image data record which features the greatest similarity to an image object in the second 3D image data record. Provision can however also be made for the most suitable 3D image data record to be manually selected for instance by means of an operating person. It is then ensured that the second 3D image data record is only extended and/or amended by such data which also corresponds to the actually existing real situation.

First data is preferably selected in the at least one first 3D image data record provided, in particular by way of a binary segmentation, which can be assigned to a specific biological tissue type of the biological object and in which obtained second 3D image data record, second data is selected, in particular by way of a binary segmentation, which can be assigned to the same biological tissue type. In step c), the image registration preferably then takes place with the aid of the first and second data. For instance, provision can be made for the first and second data to be selected such that it corresponds to bone material of the biological object if the biological object includes bone material and soft tissue. Then, in step c), the image registration can be implemented in two stages, wherein in a first stage, an image registration takes place with the aid of the first and second data assigned to the bone material and in a second stage downstream of the first stage, a refined image registration takes place with the aid of the data of the first and second image data record, which are assigned to the soft tissue. A particularly precise and reliable image registration is ensured in this way, thereby rendering possible a correct extension and amendment of the data of the second 3D image data record.

An inventive computed tomograph includes an x-ray source, a detector and an image evaluation apparatus, which is embodied to execute the inventive method. The computed tomograph may in particular include an x-ray C-arm and be embodied as a PET/CT system. Provision can in particular also be made for the detector to be embodied as a flat panel detector. The method is then particularly effective for suppressing the aliasing artifacts overlapping the field of view.

The preferred embodiments represented with reference to the inventive method and their advantages apply accordingly to the inventive computed tomographs.

BRIEF DESCRIPTION OF THE DRAWINGS

The invention is explained in more detail below with reference to exemplary embodiments, in which:

FIG. 1 shows a schematic representation of an x-ray C-arm computed tomograph; and FIG. 2 shows a schematic illustration of an exemplary embodiment of the inventive method.

DETAILED DESCRIPTION OF INVENTION

Identical or functionally identical elements are provided with the same reference characters in the figures.

FIG. 1 shows a computed tomograph 10 with an x-ray C-arm 18, to one end of which an x-ray source 12 is fastened which emits x-ray radiation S in the direction of an x-ray detector 14. A patient 16 is arranged on a couch between the x-ray source 12 and the x-ray detector 14, wherein a body part of the patient is irradiated by the x-ray radiation S.

The x-ray C-arm 18 is embodied to be rotatable and can in this way detect the body part of the patient 16 from different perspectives or at different angles. In this way, different x-ray projection images can be detected by way of the x-ray detector 14, which are transferred by way of a computer 20. A 3D image data record 28 can be reconstructed from the projection images by way of a method for back projection. The 3D image data record 28 of the body part is shown schematically in FIG. 2. In the exemplary embodiment, the body part is an arm 22 of the patient 16. The arm 22 is only detected in one subarea 32 and thus incompletely on account of the restricted view field of the x-ray source 12 and x-ray detector 14. In the exemplary embodiment, the hand is almost partially truncated. The capture area S1 does not cover the arm 22 completely. If a 3D image is generated from the 3D image data record 28, e.g. by means of forward projection, this indicates aliasing artifacts overlapping the field of view or truncation artifacts on account of the truncated hand.

A method is therefore proposed, with the aid of which missing information in the defective 3D image data record 28 can be extended. Statistical shape models of anatomical structures are used here. Such a model is formed by a 3D master image 26 of the arm 22. The 3D master image 26 covers a larger subarea 34 of the arm 22 than the 3D image data record 28. Such a statistical shape model may be generated on the arm 22 (or on a hip or a shoulder region for instance) such that information from various recorded and segmented computed tomography data records are used. Provision is made for the 3D master image 26 to exist in a database 24 in the computer 20. Different computed tomography data records of the respective anatomical regions may exist here.

Within the scope of a binary segmentation, bones and soft tissue material are initially separated from one another. The result of this segmentation provides data records, which minor surface forms and are stored in the database. Different methods can be used to generate the surface, like for instance thin plate splines or surface morphing.

A similar segmentation to the 3D master image 26 is also implemented on the 3D image data record 28. Image areas, which can be assigned to bone material, can in this way similarly be distinguished from image areas which correspond to the soft tissue.

A 3D-3D image registration then takes place automatically or manually between the 3D image data record 28 and the 3D master image 26. The image areas, which correspond to the bone material, are used here as a first match criterion for the image registration. An adjustment by means of the image areas, which correspond to the soft tissue, can take place in a second step within the scope of a refined image registration. This image registration takes place in step R.

Within the scope of this image registration, the 3D master image 26 stored in the database 24 can be adjusted to the subarea 32 in the 3D image data record 32 within the scope of a deformation method (e.g. thin-plates spline-warping) such that a good match is achieved.

A modified 3D image data record is produced, in which the original area S1 of the 3D image data record 28 is extended to an area S2 on account of the additional information of the 3D master image 26. The subarea 32 of the 3D image data record 28 is herewith extended by the extension area 36, which results from the subarea 34 of the 3D master image. As a result, the modified 3D image data record 30 is achieved.

The thus resulting modified 3D image data record 30 can now be projected forwards so that a projection image results in which the aliasing artifacts overlapping the field of view are suppressed. The thus obtained computed tomography image can also be smoothed by way of a histogram analysis, so that the image quality is improved.

The presented method is advantageous in that very defective or noisy x-ray image data can be significantly improved in respect of their quality by the statistic shape model. The 3D master image 26 provides anatomically correct data, by means of which a very precise extrapolation of the 3D image data record 28 is possible. Extrapolation methods known from the prior art must instead be based here on water ellipsoids for instance, since no anatomical information exists in the truncation area. The shape and design of the patient can now be precisely considered. Additional sensors are not necessary.

The invention claimed is:

1. A method for providing a 3D image data record of a biological object with a suppressed aliasing artifact overlapping a field of view, wherein an aliasing artifact overlapping the field of view is caused by an incomplete geometric capture of the biological object by a computed tomograph, comprising:
   providing a first 3D image data record describing a subarea of the biological object;
   obtaining a second 3D image data record of the biological object by the computed tomograph, wherein the second 3D image data record includes data relating to the subarea of the biological object described by the first 3D image data record;
   registering the first 3D image data record with the second 3D image data record;
   extending and/or amending data of the second 3D image data record as a function of data of the first 3D image data record so that a part of the data of the second 3D image data record can be assigned to the aliasing artifact overlapping the field of view; and
   generating a modified second 3D image data record with the suppressed aliasing artifact overlapping the field of view,
   wherein the first 3D image data record is registered with the second 3D image data record by:
      positionally and dimensionally assigning the data of the first 3D image data record to the data of the second 3D image data record;
      determining a degree of match between the data assigned to one another; and
      modifying the data of the first 3D image data record assigned to the data of the second 3D image data record by draw points so that the degree of match increases.

2. The method as claimed in claim 1, further comprising:
   obtaining a 2D image data record from the modified second 3D image data record, and
   generating a forward projection image and/or an x-ray sectional image from the 2D image data record.

3. The method as claimed in claim 1, wherein the first 3D image data record is provided by:
   providing at least two image data records relating to at least two comparison objects which are similar or identical to the biological object; and
   determining the first 3D image data record describing the subarea of the biological object by obtaining an averaged effective image data record from the at least two image data records.

4. The method as claimed in claim 3, wherein the at least two image data records of the at least two comparison objects are created by computed tomography images, and wherein the computed tomography images are segmented.

5. The method as claimed in claim 1, wherein the first 3D image data record is stored in a database, and wherein the database comprises at least two different 3D image data records describing different subareas of the biological object or different biological objects.

6. The method as claimed in claim 1,
   wherein a first data is selected in the first 3D image data record by a binary segmentation and is assigned to a specific type of biological tissue of the biological object,
   wherein a second data is selected in the second 3D image data record by a binary segmentation and is assigned to a same type of the biological tissue of the biological object, and
   wherein the first 3D image data record is registered with the second 3D image data record according to the first and the second data.

7. A computed tomography, comprising:
   an x-ray source;
   an x-ray detector; and
   an image evaluation apparatus adapted to execute a method comprising the steps of:
      providing a first 3D image data record describing a subarea of the biological object;
      obtaining a second 3D image data record of the biological object by the computed tomograph, wherein the second 3D image data record includes data relating to the subarea of the biological object described by the first 3D image data record;
      registering the first 3D image data record with the second 3D image data record;
      extending and/or amending data of the second 3D image data record as a function of data of the first 3D image data record so that a part of the data of the second 3D image data record can be assigned to the aliasing artifact overlapping the field of view; and generating a modified second 3D image data record with the suppressed aliasing artifact overlapping the field of view, wherein the first 3D image data record is registered with the second 3D image data record by:

positionally and dimensionally assigning the data of the first 3D image data record to the data of the second 3D image data record;

determining a degree of match between the data assigned to one another; and modifying the data of the first 3D image data record assigned to the data of the second 3D image data record by draw points so that the degree of match increases.

8. The computed tomograph as claimed in claim 7, wherein the x-ray detector is a flat panel detector.

* * * * *